United States Patent
Dulak et al.

(10) Patent No.: US 7,316,677 B1
(45) Date of Patent: Jan. 8, 2008

(54) URETERAL ACCESS SHEATH

(75) Inventors: Gary R. Dulak, Newport Beach, CA (US); Ralph V. Clayman, Irvine, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 298 days.

(21) Appl. No.: 10/198,030

(22) Filed: Jul. 17, 2002

Related U.S. Application Data

(63) Continuation-in-part of application No. 09/303,485, filed on Apr. 30, 1999, now Pat. No. 6,471,684.

(51) Int. Cl.
*A61M 25/00* (2006.01)

(52) U.S. Cl. ............... 604/523; 604/524; 604/533; 604/103

(58) Field of Classification Search ............ 604/523, 604/524, 264, 526, 164.03, 164.09, 275, 604/544, 328, 164.04, 164
See application file for complete search history.

(56) References Cited

U.S. PATENT DOCUMENTS

| | | | |
|---|---|---|---|
| 1,538,678 A | 5/1925 | Blinn | |
| 1,538,679 A | 5/1925 | Blinn | |
| 2,747,574 A | 5/1956 | DeLorenzo | |
| 3,154,074 A | 10/1964 | Harrison | |
| 3,421,509 A | 1/1969 | Fiore | |
| 3,592,197 A | 7/1971 | Cohen | |
| 4,636,199 A | 1/1987 | Victor | |
| 4,932,413 A | 6/1990 | Shockey et al. | |
| 4,942,669 A * | 7/1990 | Schnedl .................. 33/725 |
| 4,981,477 A | 1/1991 | Schon et al. | |
| D318,733 S | 7/1991 | Wyzgala | |
| 5,041,083 A | 8/1991 | Tsuchida et al. | |
| 5,131,380 A | 7/1992 | Heller et al. | |
| 5,154,005 A | 10/1992 | Lalevee, Sr. | |
| D335,710 S | 5/1993 | Ainger, III | |
| 5,344,413 A | 9/1994 | Allman et al. | |
| 5,372,592 A | 12/1994 | Gambale | |
| 5,380,304 A | 1/1995 | Parker | |

(Continued)

OTHER PUBLICATIONS

European Patent Office, Supplementary Partial European Search Report for European Patent Application No. 00931958.3, 5 pages, mailed Jun. 21, 2006.

*Primary Examiner*—Kevin C. Sirmons
*Assistant Examiner*—Phillip Gray
(74) *Attorney, Agent, or Firm*—Cynthia A. Bonner; David G. Majdali; Kenneth K. Vu

(57) ABSTRACT

A ureteral access sheath adapted for insertion into a urethra includes an elongate tube extending between a proximal end and a distal end. A handle assembly is disposed at the proximal end and includes enlarged portions which inhibit migration of the sheath into the urethra. The enlarged portions are shaped like the bell of a horn with a concave, distally-facing outer surface and a convex, proximally-facing inner surface. The inner surface functions as a funnel while the outer surface is sized and configured to receive adjacent fingers of a user's hand held in its natural position. In an associated method, this shape of the handle assembly facilitates maintaining the sheath in a stationary position during insertion and removal of instrumentation. The handle assembly can be movable on the tube to facilitate variation of the sheath link in situ.

16 Claims, 5 Drawing Sheets

U.S. PATENT DOCUMENTS

| | | |
|---|---|---|
| 5,407,441 A | 4/1995 | Greenbaum |
| 5,513,660 A | 5/1996 | Simon et al. |
| 5,531,717 A | 7/1996 | Roberto et al. |
| 5,569,159 A | 10/1996 | Anderson et al. |
| 5,620,408 A | 4/1997 | Vennes et al. |
| 5,700,253 A | 12/1997 | Parker |
| 5,718,678 A | 2/1998 | Fleming, III |
| 5,773,020 A | 6/1998 | Place et al. |
| 5,891,112 A | 4/1999 | Samson |
| 5,906,584 A | 5/1999 | Pavoni et al. |
| 6,210,358 B1 | 4/2001 | Roger |

\* cited by examiner

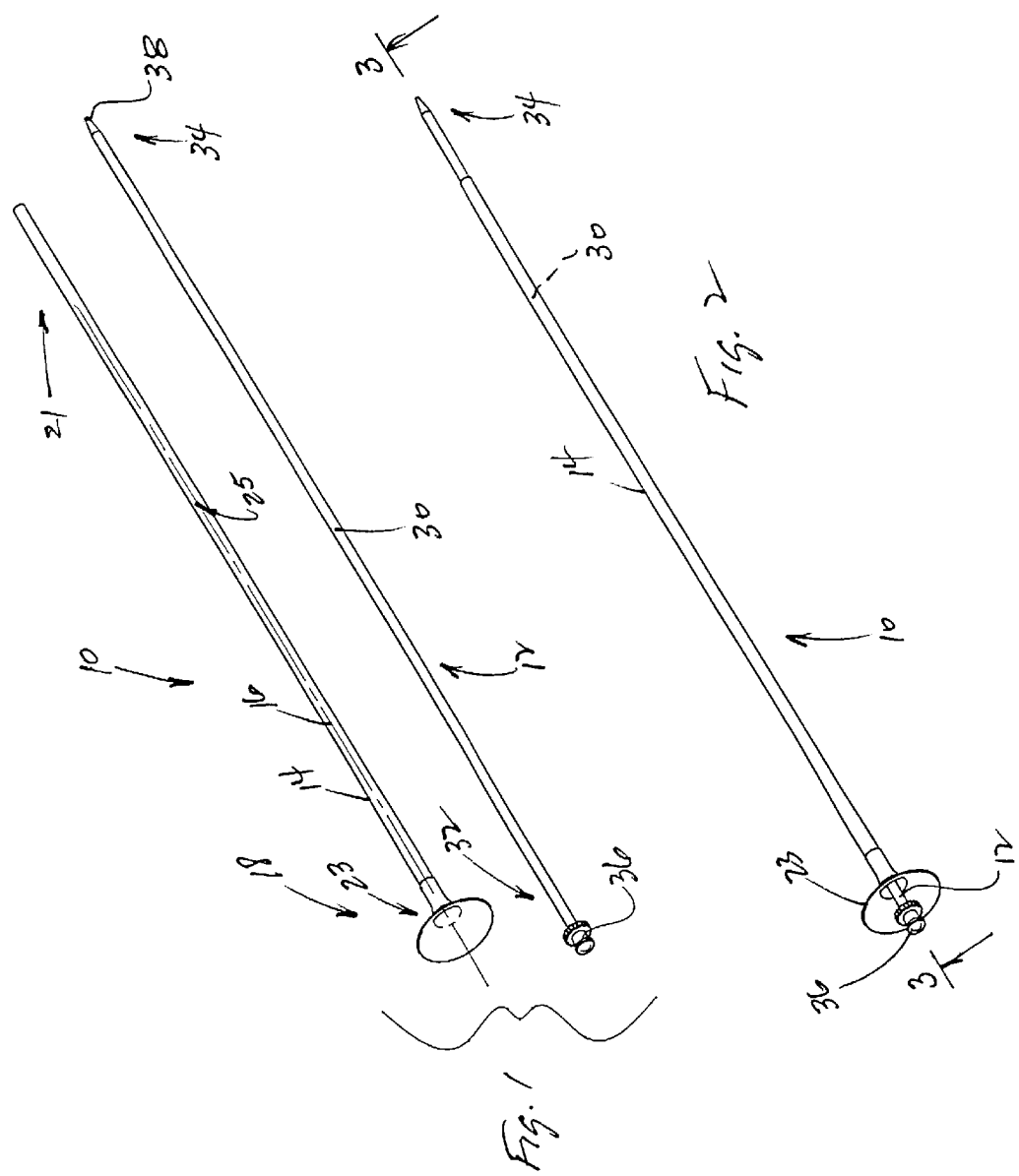

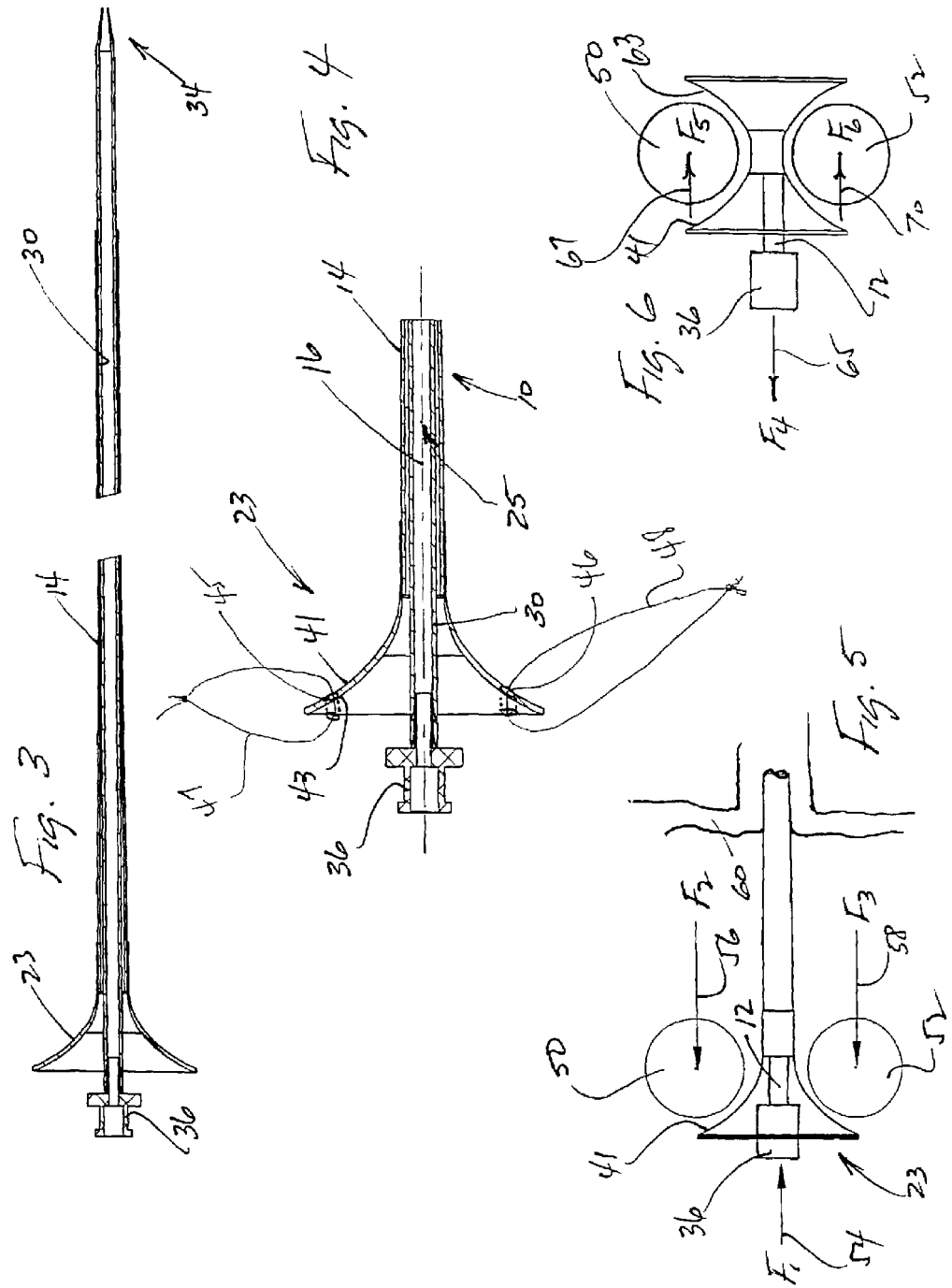

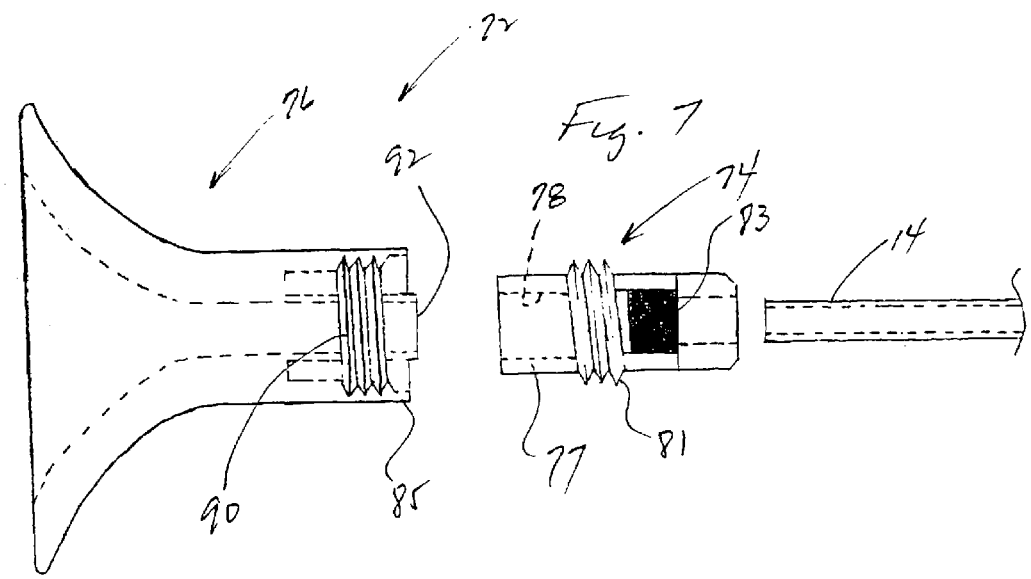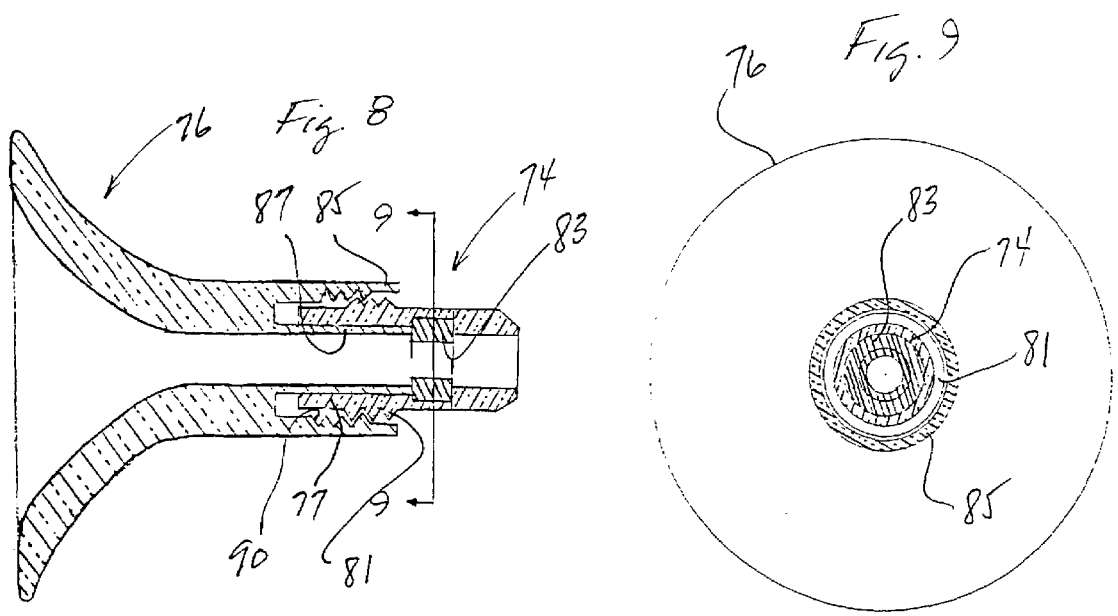

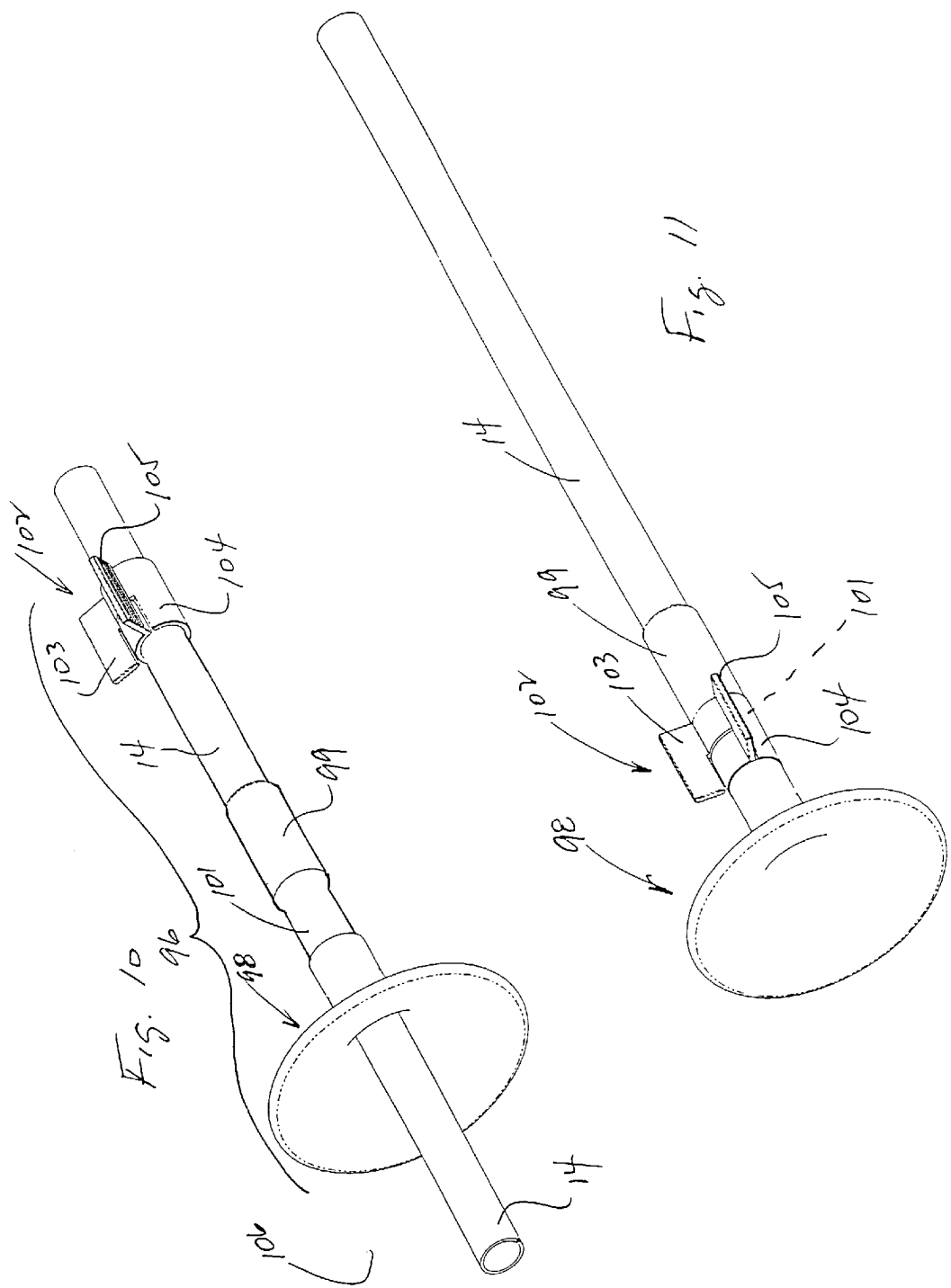

URETERAL ACCESS SHEATH

CROSS-REFERENCE TO RELATED APPLICATION

This application is a continuation-in-part of U.S. patent application Ser. No. 09/303,485, filed Apr. 30, 1999, now U.S. Pat. No. 6,471,684, the entire disclosure of which is hereby incorporated by reference as if set forth in full herein.

BACKGROUND OF THE INVENTION

1. Field of the Invention

This invention relates generally to guideways for endoluminal access and more specifically to surgical access devices adapted to introduce surgical instrumentation into body conduits.

2. Discussion of the Prior Art

Surgical access devices of the prior art typically include a sheath having an outside diameter and an inside diameter. An obturator or dilator is inserted into the sheath to facilitate introduction of the sheath into the body conduit. Once the sheath is positioned, the obturator is removed leaving a working channel for surgical instrumentation.

Particularly in the field of urology, the sheath has been provided in the form of an elongate tube having an axis extending between a proximal end and a distal end. The diameter of the tube is generally constant, except for a reduced diameter segment at the distal end. Although the obturator has had an enlarged structure at its proximal end, there has been no such enlargement for the sheath. This has presented a problem as the sheath has tended to migrate distally and disappear beneath the urethral meatus. Representative of this art is the FLEXIBLE URETEROSCOPE SHEATH manufactured and sold by Cook Urological Incorporated.

Access devices particularly adapted for other body conduits have had enlargements at the proximal end, but these have not been specifically configured to prevent migration or facilitate the introduction of instrumentation. Representative of this art are the "banana peel" sheaths which split axially for removal after catheter placement.

During the introduction and removal of dilators, obturators, and instrumentation into and out of a sheath, it is always desirable to facilitate maintenance of the sheath in a relatively stationary orientation. In the past, there has been no handle structure which was sized and shaped to accommodate engagement by a user's hand disposed in its natural position with the palm facing the user. Nor has there been any progressive funnel structure which would facilitate the introduction of instrumentation into the working channel of the sheath.

SUMMARY OF THE INVENTION

These deficiencies of the prior art have been eliminated with the present access device which includes a sheath having at its proximal end a handle specifically adapted to inhibit migration and facilitate use with instrumentation. The handle is formed as a radial enlargement having a distally-facing surface and a proximally-facing surface. The distally-facing surface has a generally concave configuration which provides a gradual enlargement inhibiting migration of the sheath into the ureter. The concave configuration is sized to receive adjacent fingers of a user's hand disposed in its natural position, in order to facilitate the stationary orientation of the sheath. The concave, distally-facing surface is continuous around the axis of the sheath so that the advantage of this concave configuration can be appreciated regardless of the radial orientation of the sheath.

The proximal-facing surface has a generally convex configuration providing for an increased funneling of an instrument as it is inserted into the working channel of the sheath. Both the distally-facing surface and the proximally-facing surface extend radially inwardly with progressively equal distal positions along the sheath. This provides the handle with the general shape of the bell of a horn. This configuration is not only ergonomically comfortable, but highly practical in addressing the problems of migration, as well as instrument insertion and removal.

The handle can be provided with characteristics permitting the handle to be moved to a preferred position along the tube of the sheath, and then to be fixed to the tube at that preferred location. This makes it possible to provide the sheath with any desired length, even after it has been inserted into the body conduit. A metal structure such as a spring, can be molded into the tube of the sheath to facilitate kink resistance.

The inner dilator can be provided with a Luerlock end, permitting attachment of a sidearm adaptor (not shown). This allows for installation of contrast during sheath placement without the need to remove the guidewire.

These and other features and advantages of the invention will become more apparent with a description of preferred embodiments and reference to the associated drawings.

DESCRIPTION OF THE DRAWINGS

FIG. 1 is a perspective view illustrating a sheath of the present invention with an obturator or dilator adapted for use with the sheath;

FIG. 2 is a perspective view illustrating the obturator operatively disposed within the sheath;

FIG. 3 is an axial cross-section view taken along lines 3-3 of FIG. 2 and illustrating the obturator operatively disposed within a tube and "handle" of the sheath;

FIG. 4 is an enlarged radial cross-section view of the handle assembly illustrated in FIG. 3;

FIG. 5 is a side-elevation view of the sheath and obturator operatively disposed in the urethra and illustrating a preferred configuration for the handle assembly of the sheath;

FIG. 6 is a side-elevation view similar to FIG. 5 of a further embodiment of the handle assembly of the present invention;

FIG. 7 is a side-elevation view partially in phantom and exploded to illustrate components of another preferred embodiment of the handle assembly providing for sheath length adjustment;

FIG. 8 is a side-elevation view illustrating the components of FIG. 7 in an assembled configuration;

FIG. 9 is a radial cross-section view taken along lines 9-9 of FIG. 8;

FIG. 10 is a perspective, disassembled view of a further embodiment of a handle assembly permitting length adjustment;

FIG. 11 is a perspective, assembled view of the components illustrated in FIG. 10.

DESCRIPTION OF PREFERRED EMBODIMENTS AND BEST MODE OF THE INVENTION

Figure 12:
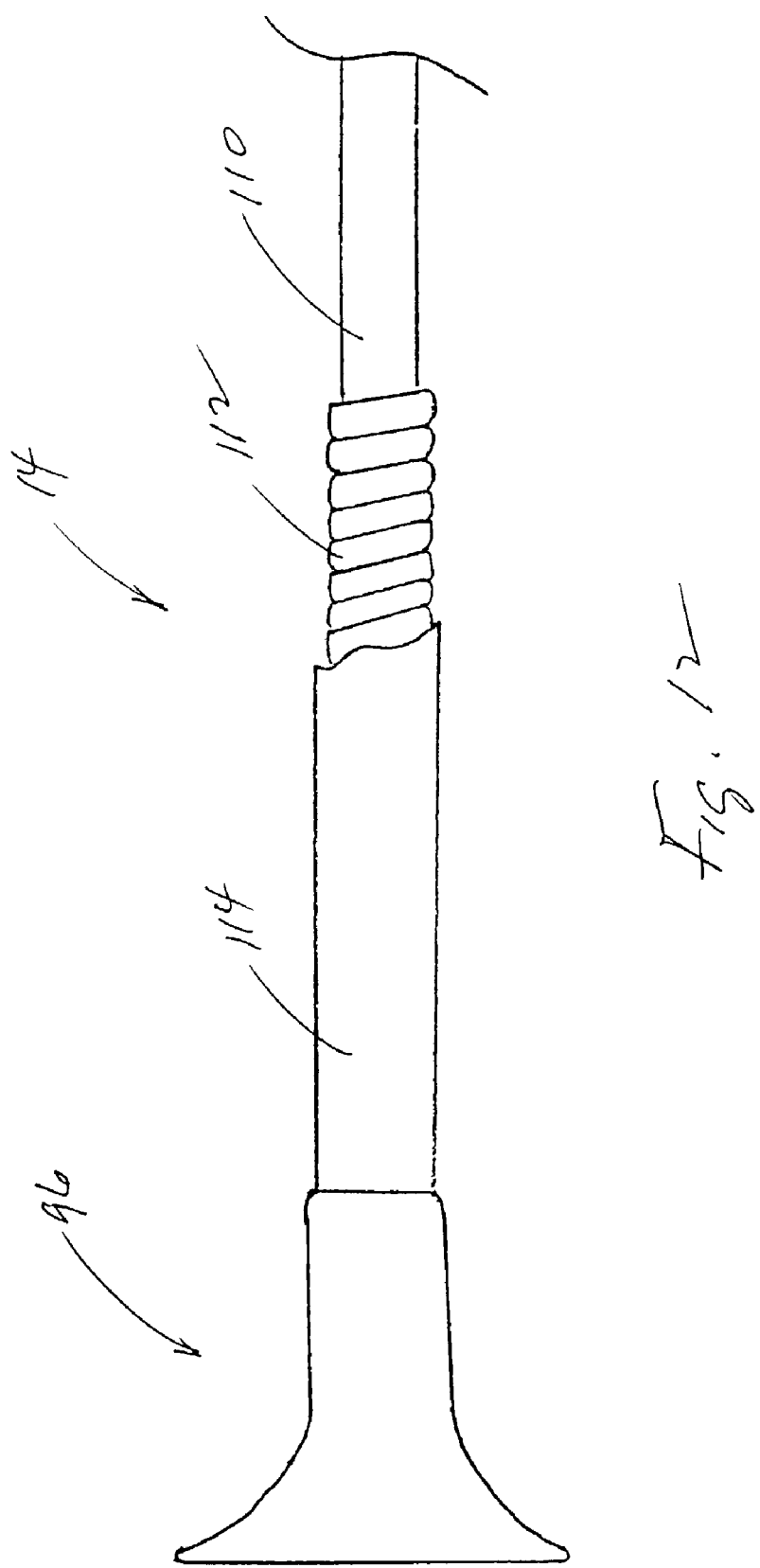
FIG. 12 is a side-elevation view partially in fragment and illustrating a spring embodiment of the tube associated with the sheath of the present invention.

A ureteral access sheath is illustrated in FIG. 1 and designated generally by the reference numeral 10. In FIG. 1, the sheath 10 is illustrated in combination with a separate, but associated, dilator or obturator 12. The sheath 10 has the general configuration of an elongate tube 14 having an axis 16 which extends between a proximal end 18 and a distal end 21. A handle 23 is disposed at the proximal end 18 of the tube 14 and provides access into a working channel 25 of the tube 14. As shown in FIG. 1, the elongate tube 14 has a first length and the handle 23 has a second length.

The obturator 12 will typically have the configuration of an elongate rod 30 extending between a proximal end 32 and a distal end 34. A knob 36 is disposed at the proximal end 32 and a tapered tip 38 is formed at the distal end 34. The obturator 12 is adapted to be inserted into the working channel 25 of the sheath 10 with the knob 36 extending proximally of the sheath 10, and the distal end 34 extending distally of the sheath 10. This operative position of the obturator 12 within the sheath 10 is illustrated in the assembled view of FIG. 2. An axial cross-section view of the assembled combination is illustrated in FIG. 3 where the rod 30 of the obturator 12 is more clearly shown within the working channel 25 of the sheath 10.

If desired, the releasable lock (not shown) can be provided to removably attach the obturator 12 to the sheath 10. When locked in place, the obturator 12 and sheath 10 can then be passed as a single unit over the guidewire. This arrangement precludes inadvertent advancement of the sheath 10 in front of the obturator 12, which could greatly impede proper passage of the sheath and potentially the ureter.

The handle 23 associated with the sheath 10 is of particular interest to the invention and is illustrated in the enlarged, axial cross-section view of FIG. 4. From this view it can be seen that the handle 23 has the general configuration of the bell of a horn. The handle 23 has a distally-facing surface 41 on the outside of the handle 23, and a proximally-facing surface 43 on the inside of the handle 23. Both of these surfaces 41 and 43 in the preferred embodiment are continuous and have a generally conical configuration. In the illustrated embodiment, the distally-facing surface 41 is generally concave, while the proximally-facing surface 43 is generally convex.

The handle 23 can be provided with two small holes 45, 46 for passage of sutures 47 and 48, respectively. Once the sheath is in place, the sutures 47, 48 can be clamped with hemostats (not shown) to the surgical drapes, thereby preventing distal migration of the sheath and loss of ureteral access. Once the obturator/sheath combination has been advanced to the desired position in the ureter, the obturator 12 can be unlocked from the sheath 10 and removed. In the manner discussed in greater detail below, these features offer particular advantages to the present invention.

One of the purposes of the proximally-facing surface 43 is to funnel the obturator 12 and other surgical instrumentation into the working channel 25 of the sheath 10. With the generally conical configuration, this proximally-facing surface functions as a funnel with a radius which decreases with progressive distal positions along the axis 16. Thus, as the instrumentation is moved distally, the proximally-facing surface 43 guides the instrument along a decreasingly decreasing radius into the working channel 25 of the sheath 10. Providing the surface 43 with a generally convex configuration further facilitates this funneling feature of the invention. When the surface 43 is convex, its radius decreases at a decreasing rate with progressively equal distal positions along the axis 16.

The distally-facing surface 41 is intended to facilitate engagement of the sheath 10 by a user's hand held in its most natural state. In FIG. 5, adjacent fingers 50 and 52 of the user's hands are illustrated schematically by the circles 50 and 52. In the natural state, the palm of the user's hands would be facing the user in the proximal direction, to the left in FIG. 5. The sheath 10 is adapted to be operatively positioned between the fingers 50 and 52 with the handle 23 positioned so that the distally-facing surface 41 is in juxtaposition to the fingers 50 and 52. This fit is facilitated by forming the surface 41 with a size and configuration generally similar to the fingers 50 and 52, as illustrated in FIG. 5. Thus, with the distally-facing surface 41 having a generally conical configuration, it has a radius which decreases with progressive distal positions along the axis 16. In an embodiment wherein the surface 41 is also concave, the radius of the surface 41 decreases at a decreasing rate with progressively equal distal positions along the axis 16.

In operation, as the surgical instrument, such as the obturator 12, is inserted into the handle 23, it produces a force $F_1$ (illustrated by arrow 54) in the distal direction. This force is opposed by the fingers 50 and 52, which engage the distally-facing surface 41 and apply opposing forces $F_2$ and $F_3$ (represented by arrows 56 and 58). In this manner, the fingers 50 and 52 can maintain the sheath 10 generally stationary even when the obturator 12 is being inserted. It will also be noted that with the user's hand in the natural position, it tends to form a barrier which prevents any instrumentation from extending exteriorly beyond the handle 23 into contact with ureteral tissue 60. As shown in FIG. 5, the urethra has a first diameter. The tube 14 has a second diameter that is less than the first diameter of the urethra while the handle 23 has a third diameter greater than the first diameter of the urethra.

Although the embodiment of FIG. 5 is particularly adapted to facilitate insertion of a surgical instrument, such as the obturator 12, it will be appreciated that removal of the instrument also creates withdrawal forces on the sheath 10. A further embodiment of the handle which can easily accommodate not only insertion forces but also withdrawal forces, is illustrated in FIG. 6. In this embodiment, a handle 61 is similar to the handle 23, except that the outer, distally-facing surface 41 is curved distally outwardly to form a proximally-facing outer surface 63. In this case, the two surfaces 41 and 63 form a continuous surface which defines an annular recess sized and configured to receive the fingers 50 and 52.

In this embodiment, insertion of the instrument, such as the obturator 12, is resisted by the forces $F_2$ and $F_3$ applied by the fingers 50 and 52, respectively, to the distally-facing surface 43, as previously discussed with reference to FIG. 5. In a similar manner, when the instrument such as the obturator 12 is withdrawn, it produces a force $F_4$ (illustrated by arrow 65) which must be resisted in order to maintain the sheath 10 stationary. This resistance is provided in the embodiment of FIG. 6 by the pressure of the fingers 50, 52 against the proximally-facing outer surface 63. Thus, fingers 50, 52 provide opposing forces $F_5$ and $F_6$ designated by arrows 67, 70, respectively.

FIGS. 7-9 illustrated a further embodiment involving a handle, such as the handles 23 or 61, which is movable relative to the tube 14 of the sheath 10. This embodiment is particularly desirable as it permits the tube 14 to be cut in situ, at the operative site, to a preferred length. With a sheath of this type, only a single access device need be present at the operative site. Multiple sheaths having different lengths are not required to be present in order to have a sheath of the desired length. As illustrated in FIG. 7, this embodiment of the sheath 10 includes the tube 14 which is slidingly engageable by a handle assembly 72 that includes a sleeve 74 and a funnel 76. The sleeve 74 is formed as a cylinder 77 having an interior bore 78 and external threads 81. An elastomeric element 83 is disposed within the bore 78 and is provided with an axial lumen 84 appropriately sized to receive the tube 14.

The funnel 76 is formed similar to the handle 23, but includes two concentric cylinders 85 and 87 which extend distally. The outer cylinder 85 is provided with interior threads 90, which are sized to receive the external threads 81 of the sleeve 74. The inner cylinder 87 of the funnel 76 is provided with an outer diameter less than the inner diameter of the bore 78. This inner cylinder 87 extends to a distal surface 92.

In operation, the funnel 76 is moved axially over the sleeve 74 and the internal threads 90 are screwed onto the external threads 81. Further rotation of the funnel 76 relative to the sleeve 74, causes the distal surface 92 of the inner cylinder 87 to axially compress the elastomeric element 83. This compression causes the element 83 to expand inwardly decreasing the diameter of its lumen 84 and thereby increasing the frictional engagement of the handle assembly 72 relative to the tube 14.

In order to provide the sheath 10 with a desired length, the tube 14 can be cut to a predetermined length, either before or after mounting the handle assembly 72 on the tube 14. Axial movement of the handle assembly 72 to a desired proximal location on the tube 14 provides the sheath 10 with the desired length. Operation of the handle 72 in the manner previously discussed will fix the assembly 72 on the tube 14 at this desired location.

In another embodiment illustrated in FIG. 10, a movable handle assembly 96 includes a funnel 98 similar to the handle 23. It also includes a cylinder 99 which extends distally within portions 101 which have a reduced diameter. A separate finger clamp 102 includes a cylinder 104 which has a diameter which is dependent upon operation of finger tabs 103 and 105. When these tabs 103 and 105 are compressed, the cylinder 104 has a relatively large diameter. When the tabs 103 and 105 are not compressed, the cylinder 104 is biased toward a reduced diameter. This finger clamp 102 is intended to be operatively disposed over the thin portions 101 of the cylinder 99, as illustrated in FIG. 11. In this operative position, the entire handle assembly 96 can be moved along the tube 14 by compressing the finger tabs 103 and 105 of the clamp 102. The tube 14 can then be cut, for example, with scissors 106, to any desired length. Compressing the finger tabs 103 and 105 will permit the handle assembly 96 to be moved to a distal position, as illustrated in FIG. 11, where the tabs 103 and 105 can be released to compress the thin portions 101 and maintain the handle assembly 96 in a fixed relationship with the tube 14.

A further embodiment of the invention is illustrated in the side-view of FIG. 12. In this embodiment, the tube 14 is formed with an inner plastic body 110, surrounded by a metal spring coil 112, which is further covered by an outer body 114. This particular embodiment of the tube 14 provides a high degree of kink resistance and can be used with any of the handle assemblies previously discussed. With this embodiment of the tube 14, the inner body 110 provides a smooth surface within the sheath 10, which facilitates passage of instrumentation. The spring coil 112 adds kink resistance to the tube 14, while the outer body 114 provides a suitable covering for the coils of the spring.

From the foregoing description of preferred embodiments, it will be apparent that many variations on the concept of this invention will be contemplated by those skilled in the art. For example, many different configurations of the tube 14 can be used with the various handle assemblies disclosed. Furthermore, the handle assemblies can be embodied in many different forms to provide at least one curved outer surface which is sized and configured to receive the fingers of a user's hand in a normal position. The fact that this desired outer shape can be combined with a funnel configuration at the proximal end of the sheath, will add further advantages to these various embodiments.

Although exemplary embodiments of the invention have been shown and described, many other changes, modifications, and substitutions will now be apparent to those of ordinary skill in the art, without necessarily departing from the spirit and scope of this invention as set forth in the following claims.

The invention claimed is:

1. A handle adapted for use with a surgical access device having a flexible elongate tube with a working channel and an axis, the handle comprising:
   a distally facing, concave surface defining radii which decrease at a decreasing rate with progressively equal distal positions along the axis;
   a first proximally facing, convex surface that is substantially parallel to the distally facing, concave surface; and
   a second proximally facing, concave surface distal to the distally facing, concave surface, the second proximally facing, concave surface being continuous with the distally facing, concave surface to define an annular recess,
   wherein the annular recess is continuous around the axis of the tube along the entire length of the annular recess.

2. The handle recited in claim 1, wherein the distally facing surface is curved substantially throughout its entirety.

3. The handle assembly recited in claim 2, wherein the first proximally facing surface is curved substantially throughout its entirety.

4. A ureteral access sheath adapted for insertion into a urethra having a diameter $D_1$, the access sheath being adapted for use by a person having a pair of adjacent fingers, the access sheath comprising:
   an elongate tube having a diameter $D_2$ and a lumen extending between a proximal end and a distal end, the diameter $D_2$ being smaller than the diameter $D_1$ of the urethra;
   a first handle disposed at the proximal end of the tube;
   portions of the first handle extending radially outwardly of the tube to provide the first handle with a diameter $D_3$ that is greater than the diameter $D_1$ of the urethra, the handle portions being defined by a first surface facing generally distally and a second surface facing generally proximally; and
   a second handle disposed distally of the first handle, the second handle including a third surface facing generally proximally,
   wherein the first surface and the third surface are concave and continuous so as to define an annular recess, sized and configured to receive the adjacent fingers of the user and continuous around the axis of the tube along the entire length of the annular recess,
   wherein the second surface is convex so as to form a funnel leading into the lumen of the tube, whereby the handle portions inhibit distal migration of the proximal end of the tube into the urethra.

5. The access sheath recited in claim 4, wherein the second surface extends decreasingly radially inwardly with progressive equal distal positions along the tube.

6. The access sheath recited in claim 5, wherein the first surface extends decreasingly radially inwardly with progressive equal distal positions along the tube.

7. The ureteral access sheath of claim 4, the elongate tube comprising a flexible elongate tube.

8. The ureteral access sheath of claim 4, wherein the elongate tube is nonmetallic.

9. A handle adapted for use with a surgical access device having an elongate flexible tube with a length $L_1$, a working channel and an axis, the handle comprising:
   a distally facing, concave surface defining radii which decrease at a decreasing rate with progressively equal distal positions along the axis;
   a first proximally facing, convex surface that is substantially parallel to the distally facing, concave surface; and
   a second proximally facing, concave surface distal to the distally facing, concave surface, the second proximally facing, concave surface being continuous with the distally facing, concave surface to define an annular recess,
   wherein the handle has a length $L_2$, which is less than $L_1$.

10. The handle recited in claim 9, wherein the distally facing surface is curved substantially throughout its entirety.

11. The handle assembly recited in claim 10, wherein the first proximally facing surface is curved substantially throughout its entirety.

12. The ureteral access sheath of claim 9, wherein the annual recess is continuous around the axis of the tube along the entire length of the annular recess.

13. The ureteral access sheath of claim 9, wherein the elongate tube is nonmetallic.

14. A ureteral access sheath adapted for insertion into a urethra having a diameter $D_1$, the access sheath being adapted for use by a person having a pair of adjacent fingers, the access sheath comprising:
   a flexible elongate tube having a length $L_1$, a diameter $D_2$ and a lumen extending between a proximal end and a distal end, the diameter $D_2$ being smaller than the diameter $D_1$ of the urethra;
   a first handle having a length $L_2$ and disposed at the proximal end of the tube;
   portions of the first handle extending radially outwardly of the tube to provide the first handle with a diameter $D_3$ that is greater than the diameter $D_1$ of the urethra, the handle portions being defined by a first surface facing generally distally and a second surface facing generally proximally; and
   a second handle having a length $L_3$ and disposed distally of the first handle, the second handle including a third surface facing generally proximally,
   wherein the combined length of the first handle and the second handle ($L_2+L_3$) is less than the length $L_1$ of the elongate tube,
   wherein the first surface and the third surface are concave, continuous around an axis of the tube, and both sized and configured to receive the adjacent fingers of the user,
   wherein the first surface is continuous with the third surface so as to define an annular recess,
   wherein the second surface is convex so as to form a funnel leading into the lumen of the tube,
   whereby the handle portions inhibit distal migration of the proximal end of the tube into the urethra.

15. The access sheath recited in claim 14, wherein the second surface extends decreasingly radially inwardly with progressive equal distal positions along the tube.

16. The access sheath recited in claim 15, wherein the first surface extends decreasingly radially inwardly with progressive equal distal positions along the tube.

* * * * *